United States Patent
Deaver et al.

(10) Patent No.: US 10,806,731 B2
(45) Date of Patent: *Oct. 20, 2020

(54) COMPOSITIONS OF BUPRENORPHINE AND μ ANTAGONISTS

(71) Applicant: Alkermes Pharma Ireland Limited, Dublin (IE)

(72) Inventors: Daniel R. Deaver, Wilmington, NC (US); Elliot Ehrich, Boston, MA (US)

(73) Assignee: Alkermes Pharma Ireland Limited, Ireland (IE)

( * ) Notice: Subject to any disclaimer, the term of this patent is extended or adjusted under 35 U.S.C. 154(b) by 0 days.

This patent is subject to a terminal disclaimer.

(21) Appl. No.: 16/394,524

(22) Filed: Apr. 25, 2019

(65) Prior Publication Data
US 2019/0247387 A1    Aug. 15, 2019

Related U.S. Application Data

(60) Division of application No. 15/718,139, filed on Sep. 28, 2017, now Pat. No. 10,314,838, which is a continuation of application No. 15/066,567, filed on Mar. 10, 2016, now Pat. No. 9,918,978, which is a continuation of application No. 14/445,407, filed on Jul. 29, 2014, now Pat. No. 9,498,474, which is a division of application No. 13/715,198, filed on Dec. 14, 2012, now Pat. No. 8,822,488.

(60) Provisional application No. 61/576,233, filed on Dec. 15, 2011.

(51) Int. Cl.
| A61K 31/4748 | (2006.01) |
| A61K 45/06 | (2006.01) |
| A61K 31/485 | (2006.01) |
| A61K 9/00 | (2006.01) |

(52) U.S. Cl.
CPC ........ *A61K 31/4748* (2013.01); *A61K 9/0053* (2013.01); *A61K 9/0056* (2013.01); *A61K 31/485* (2013.01); *A61K 45/06* (2013.01); *A61K 2300/00* (2013.01)

(58) Field of Classification Search
CPC .................................................. A61K 31/485
USPC ....................................................... 514/282
See application file for complete search history.

(56) References Cited

U.S. PATENT DOCUMENTS

| 8,354,535 | B2 | 1/2013 | Kautz et al. | |
| 9,211,293 | B2 | 12/2015 | Deaver | |
| 9,498,474 | B2 * | 11/2016 | Deaver | A61K 31/4748 |
| 9,656,961 | B2 | 5/2017 | Blumberg et al. | |
| 9,913,837 | B2 | 3/2018 | Deaver et al. | |
| 9,918,978 | B2 * | 3/2018 | Deaver | A61K 45/06 |
| 10,314,838 | B2 * | 6/2019 | Deaver | A61K 9/0056 |
| 2003/0181475 | A1 | 9/2003 | Kaiko et al. | |
| 2006/0063792 | A1 | 3/2006 | Dolle et al. | |
| 2009/0311347 | A1 | 12/2009 | Oronsky et al. | |
| 2010/0240691 | A1 | 9/2010 | Turncliff et al. | |
| 2011/0034479 | A1 | 2/2011 | Dhanoa | |
| 2011/0136848 | A1 | 6/2011 | Silverman | |

FOREIGN PATENT DOCUMENTS

| JP | 60146824 A | 8/1985 |
| JP | 2015505853 A | 2/2015 |
| WO | 2011068594 A1 | 6/2011 |

OTHER PUBLICATIONS

Database Registry [Online] Chemical Abstracts Service, Columbus, Ohio, US; Jun. 21, 2005 (Jun. 21, 2005), retrieved from STN accession No. 852626-89-2 Database accession No. 852626-89-2.
"Alkermes Initiates Clinical Study of ALKS 5461 for Treatment-Resistant Depression", Business Wire, [retrieved on Jun. 5, 2015]. Retrieved from the Internet: < URL: http://www.businesswire.com/news/home/20110615005342/en/Alkermes-Initiates-Clinical-Study-ALKS-5461-Treatment-Resistant >. Jun. 15, 2011, [online], Jul. 15, 2011.
"Alkermes: Alkermes Initiates Clinical Study of ALKS 5461 for Treatment-Resistant Depression", Retrieved from the Internet: URL:http://www.pipelinereview.com/index.php/2011061543028/Neurology-and-Psychiatry/A lkermes-Initiates-Clinical-Study-of-ALKS-5461-for-Treatment-Resistant-Depression.html [retrieved on Mar. 14, 2013], Jun. 15, 2011.
"Alkermes: Strong results for Alkermes' ALKS 5461 in major depressive disorder" Retrieved from the Internet: URL:http://www.thepharmaletter.com/file/109997/strong-results-for-alkermes-alks-5461-in-major-depressive-disorder. html [retrieved on Mar. 14, 2013], Jan. 4, 2012.
Anderson, A. K. et al., "Disassociating Intensity from Valence as Sensory Inputs to Emotion", Neuron, 39(4), 2003, 581-583.
Berrocoso, E. et al., "Opiates as Antidepressants", Current Pharmaceutical Design 15, 2009, 1612-1622.
Bodkin, J. A. et al., "Buprenorphine Treatment of Refractory Depression", Journal of Clinical Psychopharmacology, 15(1) 1995, 49-57.
Callaway, E. "Buprenorphine for Depression: The Un-adoptable Orphan", Society of Biological Psychiatry, 39, 1996, 989-990.
Davis, M. P. et al., "Opioid Receptors and Opioid Pharmacodynamics", Chapter 1, 2009, 1-27.

(Continued)

*Primary Examiner* — Kevin E Weddington
(74) *Attorney, Agent, or Firm* — Elmore Patent Law Group, P.C.; Carolyn Elmore; Joseph Zucchero

(57) ABSTRACT

The invention relates to a composition comprising buprenorphine and a μ opioid receptor antagonist, wherein the composition is characterized by an Agonist Antagonist Activity Index (AAnAI) of between about 0.7 and about 2.2; wherein;

$$AAnAI = \frac{[C_{max(BUP)} / EC_{50}]}{[C_{max(ANTAGONIST)} / IC_{50}]}.$$

20 Claims, 7 Drawing Sheets

(56) References Cited

OTHER PUBLICATIONS

Eisenberger, N. et al., "Does Rejection Hurt? An fMRI Study of Social Exclusion", Science, vol. 32, 2003, 290-292.

Emrich, H. M., "Current Perspectives in the Pharmacopsychiatry of Depression and Mania", Neuropharmacology, 22(36), 1983, 385-388.

Fallon, J. H. et al., "Distribution of Dynorphin and Enkephalin Peptides in the Rat Brain", The Journal of Comparative Neurology, 249, 1986, 293-336.

Gibson, T. B. et al., "Cost Burden of Treatment Resistance in Patients with Depression", Am J Manag Care, 16(5), 2010, 370-377.

Horvitz, J. C. et al., "Dopamine D2 Receptor Blockade Reduces Response Likelihood but Does Not Affect Latency to Emit a Learned Sensory-Motor Response: Implications for Parkinson's Disease", Behavioral Neuroscience, 114(5), 2000, 934-939.

Kennedy, S. et al., "Dysregulation of Endogenous Opioid Emotion Regulation Circuitry in Major Depression in Women", Arch Gen Psychiatry, vol. 63(11), 2006, 1199-1208.

Knoll, A. T. et al., "Dynorphin, Stress, and Depression", Brain Research, 2010, 56-73.

Le, A. D. et al., "Neurobiological Processes in Alcohol Addiction", Alcoholism: Clinical and Experimental Research, 25(5): Supplement, 2001.

Liberzon, I. et al., "µ-Opioid Receptors and Limbic Responses to Aversive Emotional Stimuli", PNAS, 99(10), 2002, 7084-7089.

Machado-Viera, R. et al., "Proof of Concept Trials in Bipolar Disorder and Major Depressive Disorder: A Translational Perspective in the Search for Improved Treatments", Depress Anxiety 28(4), 2014, 267-287.

McCrimmon, D. R. et al., "On the Opiate Trail of Respiratory Depression", Am. J. Physiol Regul Integr Comp Physiol, 285, 2003, R1274-R1275.

Napier, C. et al., "Opioid Modulation of Ventral Pallidal Inputs", Annals New York Academy of Sciences, 1999, 176-201.

Pfeiffer, A. et al., "Effects of a Kappa-Opioid Agonist on Adrenocorticotropic and Diuretic Function in Man", Horm. Metabol. Res., 18(12), 1986, 842-848.

Quirarte, G. L. et al., "Norepinephrine Release in the Amygdala in Response to Footshock and Opioid Peptidergic Drugs", Brain Research, 808, 1998, 134-140.

Rothman, R. B. et al., "An open-label study of a functional opioid K antagonist in the treatment of opioid dependence", Journal of Substance Abuse Treatment, vol. 18, 2000, 277-281.

Sackeim, H. A., "The Definition and Meaning of Treatment-Resistant Depression", J Clin Psychiatry, 16, 2001, 107-17.

Shi, N-Y-R., "Genes and Functions of Opioid Peptide Receptors", Journal of Pharmacological Sciences, 130, 2007, 235-237.

Steiner, H. et al., "Role of Dynorphin and Enkephalin in the Regulation of Striatal Output Pathways and Behavior", Exp Brain Res, 123, 1998, 60-76.

Stimpson, N. et al., "Randomised Controlled Trials Investigating Pharmacological and Psychological Interventions for Treatment-Refractory Depression", British Journal of Psychiatry, 181, 2002, 284-294.

Yamamoto, T. et al., "Buprenorphine Activatesµ and Opioid Receptor Like-1 Receptors Simultaneously, but the Analgesic Effect is Mainly Mediated by µ Receptor Activation in the Rat Formalin Test", J. of Pharma and Exp Ther, vol. 318, No. 1, 2006, 206-213.

Zubieta, J. K., "Regional Mu Opioid Receptor Regulation of Sensory and Affective Dimensions of Pain", Science, vol. 293, 2001, 311-315.

Zubieta, J. K. et al., "Regulation of Human Affective Responses by Anterior Cingulate and Limbic µ-Opioid Neurotransmission", Arch Gen Psychiatry, 60(11), 2003, 1145-1153.

* cited by examiner

COMPOSITIONS OF BUPRENORPHINE AND µ ANTAGONISTS

RELATED APPLICATIONS

This application is a divisional of U.S. application Ser. No. 15/718,139, filed on Sep. 28, 2017, which is a continuation of U.S. application Ser. No. 15/066,567, filed Mar. 10, 2016, now U.S. Pat. No. 9,918,978, issued Mar. 20, 2018, which is a continuation of U.S. application Ser. No. 14/445,407, filed Jul. 29, 2014, now U.S. Pat. No. 9,498,474, issued Nov. 22, 2016, which is a divisional of U.S. application Ser. No. 13/715,198, filed Dec. 14, 2012, now U.S. Pat. No. 8,822,488, issued Sep. 2, 2014, which claims the benefit of U.S. Provisional Application No. 61/576,233, filed on Dec. 15, 2011. The entire teachings of the above applications are incorporated herein by reference.

BACKGROUND

The opioid neuropeptide system plays an important part in regulating mood disorders. [Machado-Viera R. et. al.; Depression and Anxiety, 28 (4) 2011, 267-281]. Opioid peptides and their receptors are potential candidates for the development of novel antidepressant treatment. The actions of endogenous opioids and opiates are mediated by three receptor types (µ, δ and κ), which are coupled to different intracellular effector systems. [Berrocoso E. et. al., Current Pharmaceutical Design, 15(14) 2009, 1612-22]. As such, agents that can modulate the actions of one or more of the opioid receptor types with selectivity and sensitivity are important to treat the various diseases and disorders regulated by the opioid system.

The µ-opioid system has a profound effect on emotional state and is modulated in the context of major depressive disorders (MDD) and changes in emotional state. The µ-opioid receptors are present and densely distributed in brain regions implicated in the response to stressors and the regulation and integration of emotionally significant stimuli. These include cortical regions, including the rostral anterior cingulate, prefrontal cortex [Eisenberger, Science 302, 2003, 290-2; Kennedy Arch Gen Psychiatry 63(11), 2006, 1199-208; Zubieta, Science, 293 2001, 311-5; Zubieta, Arch Gen Psychiatry, 60(11), 2003, 1145-53]. Subcortically, the µ-opioid system is known to have a prominent regulatory role in the striatopallidal pathway (nucleus accumbens, ventral pallidum) and associated circuits (e.g., amygdala, thalamus, insular cortex) involved in the evaluation and response to salient stimuli, both rewarding and nonrewarding [Anderson A K, and Sobel N. Neuron 39(4) 2003, 581-3; Horvitz J C., Behav Neurosci. 114(5), 2000, 934-9; Koob and Le Alcoholism Clinical & Experimental Research, 2001 25(5 Suppl.) 2001, 144S-151S; Napier and Mitrovic, Ann N Y Acad Sci., 1999, 176-201; Price 2000; Quirarte, Brain Res., 808(2), 1998, 134-40.; Steiner and Gerfen, Exp Brain Res., 60-76, 1998; Zubieta, Science, 293 2001, 311-5]. Activation of µ-opioid receptors increases dopamine which may contribute to anti-depressant effects including enhancement of hedonic tone and sense of contentment, but will lead also to abuse when the increase in dopamine is higher than required to treat symptoms of depression.

Positron emission tomography (PET) studies in humans have shown functional effects of the µ-opioid system in the regulation of mood. In vivo µ-opioid receptor availability in the sub-amygdalar temporal cortex has been found to inversely correlate with the metabolic responses of this region to the presentation of a negative emotional challenge [Liberzon, Proc Natl Acad Sci. 99(10): 2002, 7084-9]. In a subsequent PET study emotional challenges were shown to elicit further differences in brain µ activity between normal human subjects, patients with SSRI responsive MDD, and patients with treatment resistant depression [Kennedy, Curr. Psychiatry Rep. 8(6), 2006, 437-44].

It has been hypothesized that blockade of κ-receptor activation will have a beneficial therapeutic effect in the treatment of depression. The hypothesis is based on human and animal evidence generated primarily during the past two decades. The following discussion is adapted from a recent review by Knoll and Carlezon, Jr. [Brain Res. 2010, 56-73, 2010]. Whereas µ-opioid receptor activation results in elevation of mood in humans, activation of the κ-opioid receptor is associated with adverse effects on mood, including dysphoria and anhedonia [Pfeiffer, Horm Metab Res., 18(12): 1986, 842-8].

Anatomically, the κ-opioid receptor and dynorphin, the primary endogenous κ ligand, are expressed throughout limbic brain areas implicated in the pathophysiology of depression. In addition to dysphoria and anhedonia, some aspects of the aversive effects of κ activation appear to involve increased anxiety. κ-opioid receptors and dynorphin are expressed throughout brain areas involved in fear and anxiety, including the amygdala and extended amygdala (Alheid 2003; Fallon and Leslie 1986; Mansour, 1995b]. The effect of κ blockade in humans has yet to be tested in humans; a pharmaceutically acceptable probe has eluded medicinal chemistry efforts.

Treatment resistant depression (TRD), is a widespread disease where patients with MDD do not achieve an adequate response to monoamine reuptake inhibitor antidepressant therapy. Despite the emergence of multiple new therapeutic agents in recent decades, TRD remains a major clinical and public health problem that results in significant adverse consequences to patients, families, and society as a whole [Gibson, J., Manag. Care, 16:370-377, 2010; Sackeim, J Clin Psychiatry, 62 Suppl 16:10-17, 2001]. Prior to the advent of monoamine oxidase inhibitors (MAOIs) and tricyclic antidepressants (TCAs), opioids were the primary therapeutic modality for depression. Modern characterization of the endogenous opioid system has elaborated the role of opioidergic peptides in the regulation of both stress response behaviors and hedonic tone. Buprenorphine, a partial µ-opioid agonist, has been reported to be useful in treating depression in patients where other available therapies have failed. [Callaway, Soc. Biol. Psychiatry, 39, 1996, 989-990; Emrich et. al., Neuropharmacology, 22, 1983, 385-388; Bodkin et. al., J. Clin. Psychopharmacology, 15, 49-57, 1995].

While opioid agonists have anti-depressant effects they are generally not used to treat depression. Long-term use of a full µ-opioid agonist may result in the development of opioid-dependency in patients. In addition, there are other undesirable side effects including additive potential, sedation, respiratory depression, nausea and constipation that will accompany acute and chronic opioid use. Buprenorphine is an µ-opioid partial agonist which produces typical µ-opioid agonist effects and side effects such as additive potential and respiratory depression while producing maximal effects that are less than those of full agonists like heroin and methadone. Buprenorphine produces sufficient µ-agonist effect to enable opioid-addicted individuals to discontinue the misuse of opioids without experiencing withdrawal symptoms.

While there are many well-known opioid receptor binding compounds, there is little evidence to guide the management of depression that has not responded to a course of antidepressants. Treatment-refractory depression is an important public health problem and large pragmatic trials are needed to inform clinical practice. [Stimpson et al., The British Journal of Psychiatry, (2002) 181: 284-294]. There still remains a need to develop effective treatments of mood disorders, in particular major depressive disorders.

SUMMARY OF THE INVENTION

The invention relates to a composition comprising buprenorphine and a μ opioid receptor antagonist wherein the composition is characterized by an Agonist:Antagonist Activity Index (AAnAI) of between about 0.70 and about 2.2; wherein;

$$AAnAI = \frac{[C_{max(BUP)}/EC_{50}]}{[C_{max(ANTAGONIST)}/IC_{50}]}$$

wherein, $EC_{50}$ represents the half maximal effective serum concentration of buprenorphine, expressed as nM;

$IC_{50}$ represents the half maximal inhibitory concentration of the μ opioid antagonist in humans, expressed as nM;

$C_{max(BUP)}$ represents the peak serum or plasma concentration of buprenorphine and/or a μ opioid receptor agonist metabolite of buprenorphine, expressed as nM; and $C_{max(ANTAGONIST)}$ represents the peak serum concentration of the μ opioid antagonist and/or a μ opioid receptor antagonist metabolite of said μ opioid antagonist, expressed as nM.

The invention further relates to the treatment of depression comprising administering a composition according to the invention to a subject in need thereof.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
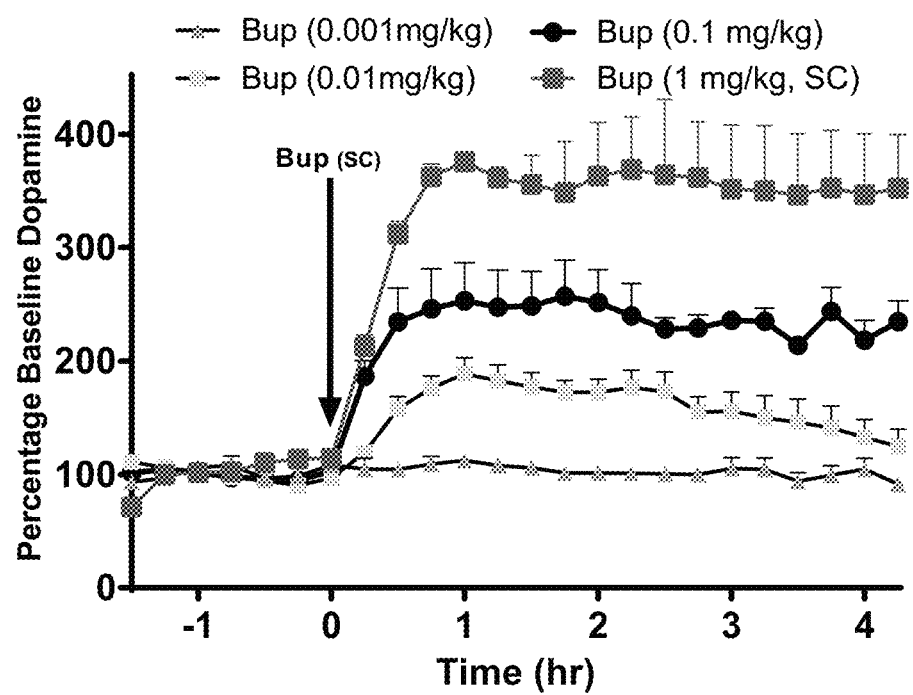
FIG. 1: Efflux of dopamine in nucleus accumbens shell after administration of buprenorphine at 0.001 mg/kg, 0.01 mg/kg, 0.1 mg/kg and 1 mg/kg doses after subcutaneous (SC) administration.

The invention relates to a composition comprising buprenorphine and another opioid receptor binding compound, wherein the opioid receptor binding compound is a μ opioid receptor antagonist, and the composition has an Agonist:Antagonist Activity Index (AAnAI) of between about 0.70 and about 2.2; wherein;

$$AAnAI = \frac{[C_{max(BUP)}/EC_{50}]}{[C_{max(ANTAGONIST)}/IC_{50}]}$$

wherein, $EC_{50}$ represents the half maximal effective serum concentration of buprenorphine, expressed as nM;

$IC_{50}$ represents the half maximal inhibitory concentration of the μ opioid antagonist in humans, expressed as nM;

$C_{max(BUP)}$ represents the peak serum or plasma concentration of buprenorphine and/or a μ opioid receptor agonist metabolite of buprenorphine, expressed as nM; and $C_{max(ANTAGONIST)}$ represents the peak serum concentration of the μ opioid antagonist and/or a μ opioid receptor antagonist metabolite of said μ opioid antagonist, expressed as nM.

Buprenorphine (BUP) was studied in combination with varying amounts of an opioid antagonist, Compound-1. This study utilized two ratios of the μ opioid receptor antagonist Compound-1 and buprenorphine, with the ratios defined by the amount of each drug (in mg) administered: a) 1:8 and b) 1:1 to evaluate safety and tolerability in patients. The 1:8 (Compound1-BUP) did show an anti-depressive effect however that change from placebo was not statistically significant. The 1:1 ratio not only proved to be better tolerated, but unexpectedly also provided a clear improvement (statistically significant and clinically meaningful versus placebo) in depression over the duration of this trial. While not wanting to be held to any particular theory, it had been thought that at the lower ratio (1:8) greater μ agonist activity would yield greater improvement in anti-depressive effects. It was an unexpected finding that less μ activity as exemplified by the higher ratio (1:1), was not only adequate to exert an anti-depressive effect, but the effects were greater than that observed with the 1:8 ratio. While the ratios above were based on mass of drug delivered, when the molecular pharmacology, systemic concentrations achieved (a function of bioavailability by the intended route and clearance) and the relative degree of agonist:antagonist activity was evaluated it was clear that a net opioid agonist activity was present at both the 1:8 and 1:1 ratios. This approach allowed for the determination of the preferred degree of balance between agonist and antagonist activity for the manifestation of an anti-depressive while eliminating the undesired effects, for example, the high associated with the addictive potential of opioids. The 1:8 ratio of Compound-1:BUP did not result in a statistical or clinically meaningful improvement in depression, and at this ratio patients still reported a "high" and sedation; the calculated "agonist:antagonist activity index" (AAnAI) was 13.4. In contrast, for the 1:1 ratio the AAnAI was 1.3. As used herein, the term "addictive potential" refers to the current Diagnostic and Statistical Manual of Mental Disorders (DSM-IV) definition for substance dependence, defined as: the ability for a compound or substance to illicit physiological dependence, evidence of tolerance or withdrawal. Without being bound to any particular theory, it is believed that to achieve the desired anti-depressive effect the preferred AAnAI is between the values of about 0.5 and 5.0, preferably about 0.7 and about 2.2. In one embodiment, the AAnAI is between about 0.6 and 4.0. In one embodiment, the AAnAI is between about 0.7 and 3.0. In a preferred embodiment, the AAnAI is between about 0.8 and about 2.1, preferably between about 1.0 and about 2.0, preferably between about 1.0 and about 1.8, preferably between about 1.1 and about 1.6, preferably between about 1.2 and about 1.4, most preferably about 1.3.

An AAnAI can be determined for buprenorphine and any compound characterized as a µ receptor antagonist. The following information is required for the µ receptor antagonist: 1) $IC_{50}$ based on GTPγS assay; and 2) $C_{max}$ concentration following dosing. For buprenorphine the following are required: 1) $EC_{50}$ based on GTPγS assay; and 2) $C_{max}$ concentrations following dosing. Other functional assays could also be used based on cAMP or other downstream end-points following receptor activation; however the GTPγS is the preferred approach. The dose yielding a $C_{max}$ value for buprenorphine or the µ opioid receptor antagonist may vary with the route of administration. Since the AAnAI is based on $C_{max}$ it can be calculated for any route of administration for the combination. Thus AAnAI is the ratio between the activities of buprenorphine and a µ receptor antagonist as shown below:

$$AAnAI = \frac{[C_{max(BUP)}/EC_{50}]}{[C_{max(ANTAGONIST)}/IC_{50}]}$$

The $EC_{50}$ and $IC_{50}$ values for buprenorphine (BUP) and Compound-1 are shown in Table-1 below. These values were determined using the GTPγS functional assay.

TABLE 1

| Buprenorphine | | Compound-1 | |
|---|---|---|---|
| $EC_{50}$ (nM) | Emax | $IC_{50}$ (nM) | Imax |
| 0.11 | 32% | 0.9 | >95% |

Plasma concentrations of buprenorphine and Compound-1 were determined in patients following the different dosing paradigms. (Table 2) The $C_{max}$ values are reported below for each drug. $C_{max}$ values are typically reported as mass/mL. These parameters reflect the potency of the buprenorphine and the µ opioid receptor antagonist.

TABLE 2

| Drug | Dose (mg) | Observed $C_{max}$ (ng/mL) | nM at $C_{max}$ | $C_{max}$/IC or $EC_{50}$ | AAnA Index |
|---|---|---|---|---|---|
| Compound-1 | 0.5 | 1.4 | 3.8 | 4.4 | 13.4 |
| BUP | 4 | 3.0 | 6.4 | 58.3 | |
| Compound-1 | 8 | 25.8 | 69.6 | 79.1 | 1.3 |
| BUP | 8 | 5.2 | 11.1 | 101.1 | |

Compound-1 $C_{max}$ ranges from 3.7 to 77× its $IC_{50}$ value for inhibiting the µ opioid receptor, while the buprenorphine $C_{max}$ ranges from about 57-99× its $EC_{50}$ as a partial agonist. At the lower ratio (1:8) the partial µ agonist activity would dominate. While at the higher ratio (1:1) the µ signaling would be greatly diminished. This agrees well with the observed clinical data. It also establishes the desired ratio that would be required for any µ antagonist in combination with BUP to treat depression while eliminating "high" and development of dependency. The desired range for this ratio, defined here as the AAnAI, would be about 0.5 to about 5 for any drug displaying antagonist activity at the µ receptor, including Compound-1, naltrexone and nalmefene. At these ratios µ signaling adequate to exert an anti-depressive effect, without the patient experiencing signs of being associated with the addictive potential of opioids, in particular buprenorphine.

The AAnAI can be calculated for any µ opioid antagonist. Naltrexone and nalmefene are two common µ opioid antagonists. In the example below, the AAnAI for naltrexone is shown for a range of $C_{max}$ values based on a dose of buprenorphine of 8 mg. Since the functional $IC_{50}$ value is 4.8 nM for naltrexone, higher $C_{max}$ values are required to achieve the same AAnAI as with Compound-1. (Table 3) Estimated dose range of naltrexone would be between 350 and 1050 mg to cover ratios of the "BUP agonist:antagonist activity" ratio of between 1 and 2.

TABLE 3

| Drug | $C_{max}$ (ng/ml) | $C_{max}$ (nM) | $C_{max}/IC_{50}$ | AAnAI |
|---|---|---|---|---|
| naltrexone | 10 | 29 | 6.1 | 16.6 |
| | 50 | 146 | 30.5 | 3.3 |
| | 100 | 293 | 61.0 | 1.7 |
| | 150 | 439 | 91.5 | 1.1 |
| | 200 | 586 | 122 | 0.8 |

In addition to differences in potency of antagonists, the ADME (Absorption, Distribution, Metabolism and Excretion) properties of the compound illustrate why a simple ratio based on the administered dose cannot be used to predict the ability of the combination of buprenorphine and an opioid antagonist to treat depression. Again using naltrexone as the example, plasma concentrations achieved with a 50 mg dose of naltrexone are illustrated. The $C_{max}$ for naltrexone is approximately 10 ng/mL. Naltrexone displays fairly dose-proportional pharmacokinetics. Consequently, the oral dose of naltrexone needed to achieve the desired AAnAI would be between about 350 and 750 mg. Importantly, to achieve the same AAnAI shown to have a clear clinical benefit for the buprenorphine-Compound-1 combination, the dose of naltrexone required would be about 625 mg and the simple ratio based on oral dose would be almost 80:1.

Similar calculations can be made for nalmefene (Table 4) based on published literature values for the $IC_{50}$ (13 nM) and reported plasma concentrations following oral administration. Based on the available literature to achieve the desired AAnAI, plasma concentrations of about 210 to 400 ng/mL are required.

TABLE 4

| Drug | $C_{max}$ (ng/ml) | $C_{max}$ (nM) | $C_{max}/IC_{50}$ | AAnAI |
|---|---|---|---|---|
| Nalmefene | 25 | 74 | 5.7 | 17.8 |
| | 100 | 295 | 22.7 | 4.5 |
| | 200 | 589 | 45.3 | 2.2 |
| | 300 | 884 | 68.0 | 1.5 |
| | 400 | 1178 | 90.7 | 1.1 |
| | 500 | 1473 | 113.3 | 0.9 |

The $IC_{50}$ for nalmefene was determined using the methods described herein and found to be more potent than previously described in the literature. The AAnAI values based on an $IC_{50}$ of 2.2 nM are provided below in Table 4A.

TABLE 4A

| Drug | $C_{max}$ (ng/ml) | $C_{max}$ (nM) | $C_{max}/IC_{50}$ | AAnAI |
|---|---|---|---|---|
| Nalmefene | 6.25 | 18.5 | 8.4 | 12.0 |
| | 12.5 | 37 | 16.8 | 6.0 |
| | 25 | 74 | 33.6 | 3.0 |
| | 100 | 295 | 134 | 0.75 |
| | 200 | 589 | 267 | 0.38 |

In some embodiments, the administration of an antagonist resulting in an AAnAI of between about 0.5 to about 5.0, preferably between about 0.7 to 2.2, modulates dopamine release. In one embodiment, the administration of a combination of buprenorphine and an antagonist of the invention results in a decrease in the production of dopamine in the nucleus accumbens shell in comparison with administration of buprenorphine alone. In a preferred embodiment, the administration of a combination of buprenorphine and Compound-1 having an activity index of between about 0.7 and about 2.2 results in a reduction in the dopamine release compared to the administration of buprenorphine alone. In a preferred embodiment, the combination of buprenorphine and an antagonist of the invention results in an average dopamine level of between about 1 pg/sample to about 2 pg/sample whereas the administration of buprenorphine alone (0.1 mg/kg) results in about 3 pg/sample after 2 hours. In one embodiment, the combination of buprenorphine and an antagonist of the invention, having an AAnAI of between about 0.7 to about 2.2, results in a reduction in dopamine release of between about 25% to about 75% in comparison with the administration of buprenorphine alone in a stimulated dopamine efflux test. Without being bound to any particular theory, the reduction in dopamine release is postulated to be useful in reducing the drug liking and addictive potential of buprenorphine, while retaining properties that contribute to an anti-depressive effect. Importantly, attenuation of μ-opioid signaling further by achieving an AAnAI of less than 0.5 would be undesirable with a loss of anti-depressive effect.

In a preferred embodiment, the μ opioid receptor antagonist is a compound of Formula I:

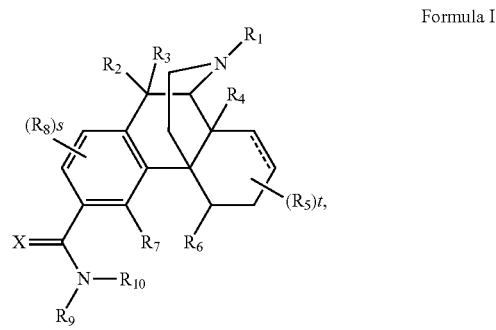

Formula I or a pharmaceutically acceptable salt, ester or prodrug thereof wherein;

s is 0, 1 or 2;

t is 0, 1, 2, 3, 4, 5, 6, or 7;

X is S or O;

$R_1$ is selected from aliphatic, substituted aliphatic, aryl, substituted aryl, heterocyclyl or substituted heterocyclyl;

each $R_2$, $R_3$, $R_4$, $R_5$, $R_6$, $R_7$ and $R_8$ is independently selected from absent, hydrogen, halogen, —$OR_{20}$, —$SR_{20}$, —$NR_{20}R_{21}$, —$C(O)R_{20}$, —$C(O)OR_{20}$, —$C(O)NR_{20}R_{21}$, —$N(R_{20})C(O)R_{21}$, —$CF_3$, —CN, —$NO_2$, —$N_3$, acyl, alkoxy, substituted alkoxy, alkylamino, substituted alkylamino, dialkylamino, substituted dialkylamino, substituted or unsubstituted alkylthio, substituted or unsubstituted alkylsulfonyl, optionally substituted aliphatic, optionally substituted aryl, heterocyclyl or substituted heterocyclyl;

each $R_9$ and $R_{10}$ is selected from hydrogen, aliphatic, substituted aliphatic, aryl, substituted aryl, heterocyclyl or substituted heterocyclyl;

alternatively, two of $R_2$, $R_3$, $R_4$, $R_5$, $R_6$, $R_7$ and $R_8$ together with the atoms they are attached to form an optionally substituted ring; alternatively $R_2$ and $R_3$ together with the carbon they are attached to form a C=X group;

wherein each $R_{20}$ and $R_{21}$ is independently selected from absent, hydrogen, halogen, —OH, —SH, —$NH_2$, —$CF_3$, —CN, —$NO_2$, —$N_3$, —C(O)OH, —$C(O)NH_2$, acyl, alkoxy, substituted alkoxy, alkylamino, substituted alkylamino, dialkylamino, substituted dialkylamino, substituted or unsubstituted alkylthio, substituted or unsubstituted alkylsulfonyl, aliphatic, substituted aliphatic, aryl or substituted aryl; and alternatively $R_9$ and $R_{10}$ together with the atom they are attached to form an optionally substituted ring; alternatively two $R_5$ groups, or an $R_5$ and an $R_6$ group, together with the carbon they are attached to form a C=X group.

In a more preferred embodiment, the μ receptor antagonist is a compound of Formula II:

Formula II

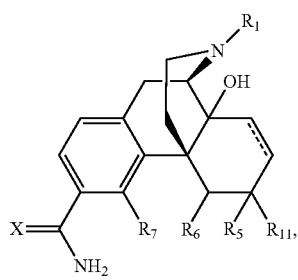

or a pharmaceutically acceptable salt, ester or prodrug thereof wherein;

X is S or O;

R₁ is —(CH₂)$_n$-c-C₃H₅, —(CH₂)$_n$-c-C₄H₇, —(CH₂)$_n$-c-C₅H₉, —(CH₂)$_n$—CH=CH₂ or —(CH₂)$_n$—CH=C(CH₃)₂ wherein n and m are independently 0, 1, 2 or 3;

R₆ and R₇ are independently H, —OH or together R₆ and R₇ form an —O— or —S— group; and R₅ and R₁₁ are independently H, —OH, OCH₃ or together R₅ and R₁ form a=O or =CH₂ group.

In a more preferred embodiment, the μ receptor antagonist is selected from:

1

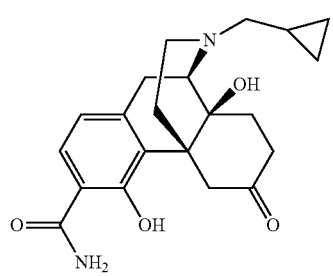

2

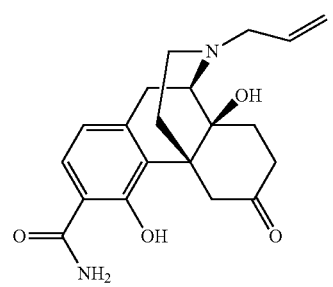

3

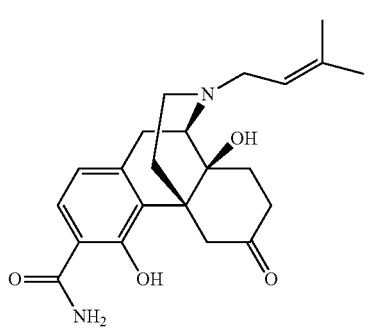

4

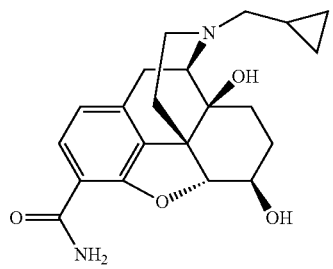

5

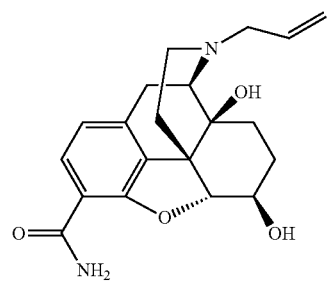

6

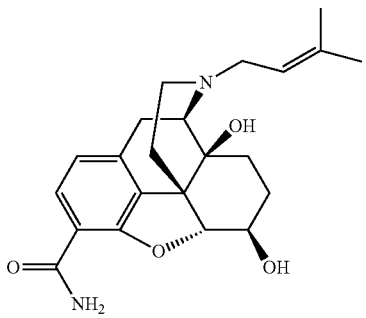

7

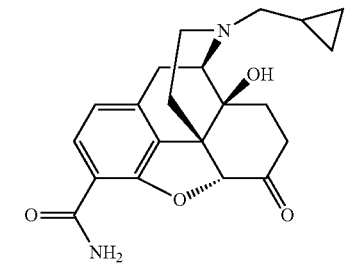

8

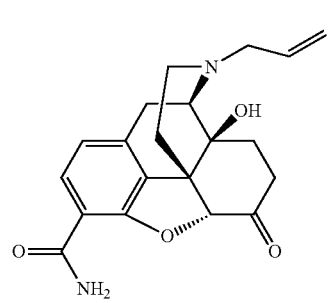

-continued

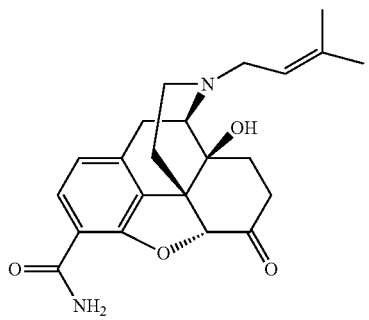
9

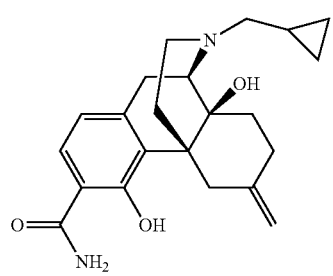
10

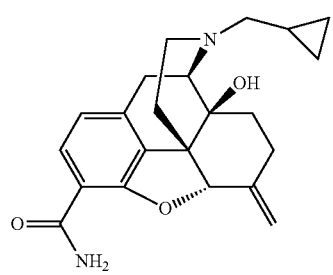
11

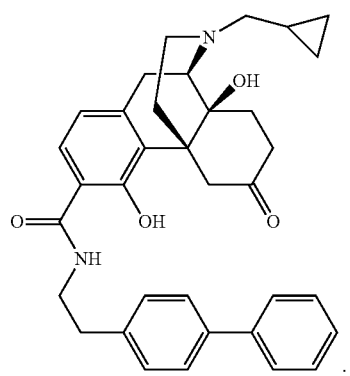
12

The invention further relates to the treatment of a depressive disorder comprising administering a composition according to the invention to a subject in need thereof. In a preferred embodiment, the depressive disorder is selected from major depressive disorder, chronic depression, severe unipolar recurrent major depressive episodes, dysthymic disorder, depressive neurosis and neurotic depression, melancholic depression, atypical depression, reactive depression, treatment resistant depression, seasonal affective disorder and pediatric depression; premenstrual syndrome, premenstrual dysphoric disorder, hot flashes, bipolar disorders or manic depression, bipolar I disorder, bipolar II disorder and cyclothymic disorder. In a preferred embodiment, the depressive disorder is a major depressive disorder. In a more preferred embodiment, the depressive disorder is treatment resistant depression.

The invention further relates to the treatment of obsessive compulsive disorder, bulimia nervosa, panic disorder, post-traumatic stress disorder (PTSD), premenstrual dysphoric disorder (PMDD), social anxiety disorder and generalized anxiety disorder (GAD).

Definitions

Listed below are definitions of various terms used to describe this invention. These definitions apply to the terms as they are used throughout this specification and claims, unless otherwise limited in specific instances, either individually or as part of a larger group.

The term "aliphatic group" or "aliphatic" refers to a non-aromatic moiety that may be saturated (e.g. single bond) or contain one or more units of unsaturation, e.g., double and/or triple bonds. An aliphatic group may be straight chained, branched or cyclic, contain carbon, hydrogen or, optionally, one or more heteroatoms and may be substituted or unsubstituted. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may include alkyl, substituted alkyl, alkenyl, substituted alkenyl, alkynyl, substituted alkynyl, and substituted or unsubstituted cycloalkyl groups as described herein.

The term "acyl" refers to a carbonyl substituted with hydrogen, alkyl, partially saturated or fully saturated cycloalkyl, partially saturated or fully saturated heterocycle, aryl, or heteroaryl. For example, acyl includes groups such as ($C_1$-$C_6$) alkanoyl (e.g., formyl, acetyl, propionyl, butyryl, valeryl, caproyl, t-butylacetyl, etc.), ($C_3$-$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

The term "alkyl" is intended to include both branched and straight chain, substituted or unsubstituted saturated aliphatic hydrocarbon radicals/groups having the specified number of carbons. Preferred alkyl groups comprise about 1 to about 24 carbon atoms ("$C_1$-$C_{24}$"). Other preferred alkyl groups comprise at about 1 to about 8 carbon atoms ("$C_1$-$C_8$") such as about 1 to about 6 carbon atoms ("$C_1$-$C_6$"), or such as about 1 to about 3 carbon atoms ("$C_1$-$C_3$"). Examples of $C_1$-$C_6$ alkyl radicals include, but are not limited to, methyl, ethyl, propyl, isopropyl, n-butyl, tert-butyl, n-pentyl, neopentyl and n-hexyl radicals.

The term "alkenyl" refers to linear or branched radicals having at least one carbon-carbon double bond. Such radicals preferably contain from about two to about twenty-four carbon atoms ("$C_2$-$C_{24}$"). Other preferred alkenyl radicals are "lower alkenyl" radicals having two to about ten carbon atoms ("$C_2$-$C_{10}$") such as ethenyl, allyl, propenyl, butenyl and 4-methylbutenyl. Preferred lower alkenyl radicals include 2 to about 6 carbon atoms ("$C_2$-$C_6$"). The terms "alkenyl", and "lower alkenyl", embrace radicals having "cis" and "trans" orientations, or alternatively, "E" and "Z" orientations.

The term "alkynyl" refers to linear or branched radicals having at least one carbon-carbon triple bond. Such radicals preferably contain from about two to about twenty-four carbon atoms ("$C_2$-$C_{24}$"). Other preferred alkynyl radicals are "lower alkynyl" radicals having two to about ten carbon atoms such as propargyl, 1-propynyl, 2-propynyl, 1-butyne, 2-butynyl and 1-pentynyl. Preferred lower alkynyl radicals include 2 to about 6 carbon atoms ("$C_2$-$C_6$").

The term "cycloalkyl" refers to saturated carbocyclic radicals having three to about twelve carbon atoms ("$C_3$-$C_{12}$"). The term "cycloalkyl" embraces saturated carbocyclic radicals having three to about twelve carbon atoms. Examples of such radicals include cyclopropyl, cyclobutyl, cyclopentyl and cyclohexyl.

The term "cycloalkenyl" refers to partially unsaturated carbocyclic radicals having three to twelve carbon atoms. Cycloalkenyl radicals that are partially unsaturated carbocyclic radicals that contain two double bonds (that may or may not be conjugated) can be called "cycloalkyldienyl". More preferred cycloalkenyl radicals are "lower cycloalkenyl" radicals having four to about eight carbon atoms. Examples of such radicals include cyclobutenyl, cyclopentenyl and cyclohexenyl.

The term "alkylene," as used herein, refers to a divalent group derived from a straight chain or branched saturated hydrocarbon chain having the specified number of carbons atoms. Examples of alkylene groups include, but are not limited to, ethylene, propylene, butylene, 3-methyl-pentylene, and 5-ethyl-hexylene.

The term "alkenylene," as used herein, denotes a divalent group derived from a straight chain or branched hydrocarbon moiety containing the specified number of carbon atoms having at least one carbon-carbon double bond. Alkenylene groups include, but are not limited to, for example, ethenylene, 2-propenylene, 2-butenylene, 1-methyl-2-buten-1-ylene, and the like.

The term "alkynylene," as used herein, denotes a divalent group derived from a straight chain or branched hydrocarbon moiety containing the specified number of carbon atoms having at least one carbon-carbon triple bond. Representative alkynylene groups include, but are not limited to, for example, propynylene, 1-butynylene, 2-methyl-3-hexynylene, and the like.

The term "alkoxy" refers to linear or branched oxy-containing radicals each having alkyl portions of one to about twenty-four carbon atoms or, preferably, one to about twelve carbon atoms. More preferred alkoxy radicals are "lower alkoxy" radicals having one to about ten carbon atoms and more preferably having one to about eight carbon atoms. Examples of such radicals include methoxy, ethoxy, propoxy, butoxy and tert-butoxy.

The term "alkoxyalkyl" refers to alkyl radicals having one or more alkoxy radicals attached to the alkyl radical, that is, to form monoalkoxyalkyl and dialkoxyalkyl radicals.

The term "aryl", alone or in combination, means an aromatic system containing one, two or three rings wherein such rings may be attached together in a pendent manner or may be fused. The term "aryl" embraces aromatic radicals such as phenyl, naphthyl, tetrahydronaphthyl, indane furanyl, quinazolinyl, pyridyl and biphenyl.

The terms "heterocyclyl", "heterocycle" "heterocyclic" or "heterocyclo" refer to saturated, partially unsaturated and unsaturated heteroatom-containing ring-shaped radicals, which can also be called "heterocyclyl", "heterocycloalkenyl" and "heteroaryl" correspondingly, where the heteroatoms may be selected from nitrogen, sulfur and oxygen. Examples of saturated heterocyclyl radicals include saturated 3 to 6-membered heteromonocyclic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. Heterocyclyl radicals may include a pentavalent nitrogen, such as in tetrazolium and pyridinium radicals. The term "heterocycle" also embraces radicals where heterocyclyl radicals are fused with aryl or cycloalkyl radicals. Examples of such fused bicyclic radicals include benzofuran, benzothiophene, and the like.

The term "heteroaryl" refers to unsaturated aromatic heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like.

The term "heterocycloalkyl" refers to heterocyclo-substituted alkyl radicals. More preferred heterocycloalkyl radicals are "lower heterocycloalkyl" radicals having one to six carbon atoms in the heterocyclo radical.

The term "alkylthio" refers to radicals containing a linear or branched alkyl radical, of one to about ten carbon atoms attached to a divalent sulfur atom. Preferred alkylthio radicals have alkyl radicals of one to about twenty-four carbon atoms or, preferably, one to about twelve carbon atoms. More preferred alkylthio radicals have alkyl radicals which are "lower alkylthio" radicals having one to about ten carbon atoms. Most preferred are alkylthio radicals having lower alkyl radicals of one to about eight carbon atoms. Examples of such lower alkylthio radicals include methylthio, ethylthio, propylthio, butylthio and hexylthio.

The terms "aralkyl" or "arylalkyl" refer to aryl-substituted alkyl radicals such as benzyl, diphenylmethyl, triphenylmethyl, phenylethyl, and diphenylethyl.

The term "aryloxy" refers to aryl radicals attached through an oxygen atom to other radicals.

The terms "aralkoxy" or "arylalkoxy" refer to aralkyl radicals attached through an oxygen atom to other radicals.

The term "aminoalkyl" refers to alkyl radicals substituted with amino radicals. Preferred aminoalkyl radicals have alkyl radicals having about one to about twenty-four carbon atoms or, preferably, one to about twelve carbon atoms. More preferred aminoalkyl radicals are "lower aminoalkyl" that have alkyl radicals having one to about ten carbon atoms. Most preferred are aminoalkyl radicals having lower alkyl radicals having one to eight carbon atoms. Examples of such radicals include aminomethyl, aminoethyl, and the like.

The term "alkylamino" denotes amino groups which are substituted with one or two alkyl radicals. Preferred alkylamino radicals have alkyl radicals having about one to about twenty carbon atoms or, preferably, one to about twelve carbon atoms. More preferred alkylamino radicals are "lower alkylamino" that have alkyl radicals having one to about ten carbon atoms. Most preferred are alkylamino radicals having lower alkyl radicals having one to about eight carbon atoms. Suitable lower alkylamino may be monosubstituted N-alkylamino or disubstituted N,N-alkylamino, such as N-methylamino, N-ethylamino, N,N-dimethylamino, N,N-diethylamino or the like.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkyl sulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the sub stituent may be further substituted.

For simplicity, chemical moieties that are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety. The terms "halogen" or "halo" as used herein, refers to an atom selected from fluorine, chlorine, bromine and iodine.

The terms "compound", "drug", and "prodrug" as used herein all include pharmaceutically acceptable salts, co-crystals, solvates, hydrates, polymorphs, enantiomers, diastereoisomers, racemates and the like of the compounds, drugs and prodrugs having the formulas as set forth herein.

Substituents indicated as attached through variable points of attachments can be attached to any available position on the ring structure.

As used herein, the term "effective amount of the subject compounds," with respect to the subject method of treatment, refers to an amount of the subject compound which, when delivered as part of desired dose regimen, brings about management of the disease or disorder to clinically acceptable standards.

"Treatment" or "treating" refers to an approach for obtaining beneficial or desired clinical results in a patient. For purposes of this invention, beneficial or desired clinical results include, but are not limited to, one or more of the following: alleviation of symptoms, diminishment of extent of a disease, stabilization (i.e., not worsening) of a state of disease, preventing occurrence or recurrence of disease, delay or slowing of disease progression, amelioration of the disease state, and remission (whether partial or total).

As used herein, the term "major depressive disorder" (MDD) is used as that term is understood in art, and refers to a diagnosis that is guided by diagnostic criteria listed in Diagnostic and Statistical Manual of Mental Disorders, Fourth Edition (DSM-IV) or ICD-10, or in similar nomenclatures.

Patients suffering from "treatment resistant depression" include (1) those who fail to respond to standard doses (i.e., significantly superior to placebo in double-blind studies) of antidepressants (such as a monoamine oxidase inhibitors (MAOIs), tricyclic antidepressants (TCAs), tetracyclic antidepressants (TeCAs), selective serotonin reuptake inhibitors (SSRIs), and serotonin-norepinephrine reuptake inhibitors (SNRIs)) administered continuously for a minimum duration of 6 weeks, and (2) those who fail to respond to standard doses of an antidepressant (such as a monoamine oxidase inhibitors (MAOIs), tricyclic antidepressants (TCAs), tetracyclic antidepressants (TeCAs), selective serotonin reuptake inhibitors (SSRIs), and serotonin-norepinephrine reuptake inhibitors (SNRIs)) (monotherapy) administered continuously for a minimum duration of 12 weeks. One criteria for determining whether a patient's depression is treatment resistant to an antidepressant is if a Clinical Global Impression-Improvement (CGI-I) score of 1 (very much improved) or 2 (much improved) is not achieved by the end of a 6, 8, or 12 week trial. The CGI-I scale is defined in Guy, W. (ed.): ECDEU Assessment Manual for Psychopharmacology, Revised, DHEW Pub. No. (ADM) 76-338, Rockville, Md., National Institute of Mental Health, 1976.

EXAMPLES

Example 1

A randomized, double-blind, placebo-controlled study was conducted evaluating the safety and tolerability of a combination of buprenorphine with Compound-1. The study was conducted in 32 adults with major depressive disorder who had an inadequate response to antidepressant therapy. In this study, subjects received a once daily sublingual dose of placebo or Compound-1-BUP at dose ratios of 1:8 or 1:1 with corresponding escalating doses of 0.25:2 mg/0.5:4 mg and 4:4 mg/8:8 mg, respectively, for 7 days.

Among the most common adverse events were dizziness, nausea, vomiting, and sedation (all of which were reported more frequently by subjects in the 1:8 ratio group (Cohort A) versus subjects in the 1:1 ratio (Cohort B) or placebo groups). For example, while about 28.5% of Cohort A reported sedation or somnolence, only 7% of Cohort B reported sedation or somnolence. The occurrence of dizziness was also significantly higher in Cohort A (57%) compared to Cohort B (29%). A summary of the most common adverse events (i.e, those reported by ≥10% of subjects in any treatment group) is provided in Table A:

TABLE A

Comparison of most common adverse events (>10% in any group) between placebo, Cohort A and Cohort B

| Adverse Event Preferred Term (N, %) | Placebo (N = 4) | Cohort A (N = 14) | Cohort B (N = 14) |
|---|---|---|---|
| Dizziness | 0 | 8 (57) | 4 (29) |
| Nausea | 1 (25) | 4 (29) | 3 (21) |
| Vomiting | 0 | 4 (29)* | 2 (14)* |
| Hyperhidrosis | 1 (25) | 2 (14) | 0 |
| Menorrhagia | 1 (25) | 0 | 0 |
| Pain in extremity | 1 (25) | 0 | 1 (7) |
| Constipation | 0 | 2 (14) | 3 (21) |
| Sedation or somnolence | 0 | 4 (28.5) | 1 (7) |
| Fatigue | 0 | 2 (14) | 1 (7) |
| Feeling abnormal | 0 | 0 | 2 (14) |
| Flushing | 0 | 2 (14) | 0 |

*One subject from each active group discontinued due to vomiting.
Cohort A: 1:8 ratio of Compound 1: Buprenorphine (0.25 mg:2 mg for days 1 to 3 and 0.5 mg:4 mg for days 4 to 7)
Cohort B: 1:1 ratio of Compound 1: Buprenorphine (4 mg:4 mg for days 1 to 3 and 8 mg:8 mg for days 4 to 7.

Efficacy was measured by changes from baseline to Day 7 in the 17-item Hamilton Rating Scale for Depression (HAM-D-17) and the Montgomery-Asberg Depression Rating Scale (MADRS). For subjects treated with Compound-1-BUP at the 1:8 and 1:1 dose ratios or placebo, mean (standard deviation) changes from baseline to day 7 in HAM-D-17 total scores were −5.0 (6.1), −6.7 (3.4), and −1.0 (4.2), respectively (p=0.032 for the 1:1 ratio versus placebo) and mean (SD) changes from baseline to day 7 in MADRS total scores were −8.5 (0.4), −11.4 (6.6), and −3.5 (5.8), respectively. See Tables B and C.

TABLE B

Comparison of treatment efficacy between placebo, Cohort A and Cohort B assessed by Hamilton Depression Rating Sacle-17 (Total Score)

| Parameter | | Placebo (PBO) | Cohort A (1:8) | Cohort B (1:1) |
|---|---|---|---|---|
| Baseline score | # subjects | N = 4 | N = 14 | N = 14 |
| | mean (SD) | 19.0 (3.2) | 17.5 (2.0) | 19.4 (2.7) |
| | median | 18.5 | 17.5 | 19.0 |
| Change from baseline at Day 7 | # subjects | N = 4 | N = 13 | N = 13 |
| | mean (SD) | −1.0 (4.2) | −5.0 (6.1) | −6.7 (3.4) |
| | median | 0 | −4.0 | −6.0 |
| Comparison of changes from baseline | | | Cohort A vs. PBO | Cohort B vs. PBO |
| | mean (SD) | | −4 (5.78) | −5.69 (3.57) |
| | P value* | | 0.337 | 0.032 |

*p value from exact Wilcoxon test
Cohort A: 1:8 ratio of Compound 1: Buprenorphine (0.25 mg:2 mg for days 1 to 3 and 0.5 mg:4 mg for days 4 to 7)
Cohort B: 1:1 ratio of Compound 1: Buprenorphine (4 mg:4 mg for days 1 to 3 and 8 mg:8 mg for days 4 to 7.

TABLE C

Comparison of treatment efficacy between placebo, Cohort A and Cohort B assessed by Montgomery-Åsberg Depression Rating Scale (Total Score)

| Parameter | | Placebo | Cohort A (1:8) | Cohort B (1:1) |
|---|---|---|---|---|
| Baseline score | # subjects | N = 4 | N = 14 | N = 14 |
| | mean (SD) | 24.5 (7.9) | 23.3 (4.1) | 26.4 (4.4) |
| | Median | 26.0 | 23.5 | 26.0 |
| Change from baseline at Day 7 | # subjects | N = 4 | N = 13 | N = 13 |
| | mean (SD) | −3.5 (5.8) | −8.5 (7.4) | −11.4 (6.6) |
| | median | −2.5 | −9.0 | −13.0 |
| Comparison of changes from baseline | | | Cohort A vs. PBO | Cohort B vs. PBO |
| | mean (SD) | | −4.96 (7.10) | −7.88 (6.41) |
| | P value* | | 0.256 | 0.054 |

Cohort A: 1:8 ratio of Compound 1: Buprenorphine (0.25 mg:2 mg for days 1 to 3 and 0.5 mg:4 mg for days 4 to 7)
Cohort B: 1:1 ratio of Compound 1: Buprenorphine (4 mg:4 mg for days 1 to 3 and 8 mg:8 mg for days 4 to 7.

Visual analog scales (VAS) were used to assess drug liking and other subjective drug effects. Subjects on active drug at the 1:8 ratio experienced greater subjective experiences of "Feeling High" (Table D) and "Feeling Sedated" (Table E) compared to the 1:1 ratio. The VAS results are reported as predose and postdose scores showing the magnitude of difference in the subjective experiences. For example, on Day 7, the predose Cohort A VAS score for "Feeling High" was 5.8 and postdose score was 32.9, showing a difference of 27.1 score before and after dosing. In case of Cohort B, the predosing VAS score was 14.5 and postdosing was 19.6 showing only an increase of 5.1. The comparison between the two cohorts shows that Cohort A experienced a significant increase in "Feeling High" after the dosing compared to Cohort B.

TABLE D

Visual analog scale (VAS) results for "feeling high"

| Timepoint | Placebo (mean[SD]) | Cohort A (1:8) (mean[SD]) | Cohort B (1:1) (mean[SD]) |
|---|---|---|---|
| Day 1 Predose | 18.0 (20.98) | 8.6 (19.58) | 9.1 (13.70) |
| Postdose | 48.0 (32.04) | 54.4 (36.63) | 29.4 (30.87) |
| Day 2 Predose | 6.8 (4.65) | 14.8 (16.97) | 22.5 (23.63) |
| Postdose | 9.0 (8.76) | 39.3 (29.40) | 31.5 (29.02) |
| Day 3 Predose | 7.3 (2.63) | 7.2 (11.35) | 22.7 (27.21) |
| Postdose | 6.3 (8.66) | 41.8 (30.31) | 35.5 (32.42) |
| Day 4 Predose | 6.3 (4.92) | 10.2 (9.94) | 17.5 (22.92) |
| Postdose | 7.8 (10.97) | 57.1 (30.21) | 19.1 (23.19) |
| Day 5 Predose | 7.3 (10.59) | 6.3 (4.52) | 15.7 (20.68) |
| Postdose | 23.8 (33.05) | 35.1 (34.95) | 19.5 (27.58) |
| Day 6 Predose | 22.8 (25.68) | 4.6 (3.29) | 15.5 (21.99) |
| Postdose | 29.3 (32.35) | 43.7 (30.21) | 22.1 (30.36) |
| Day 7 Predose | 24.5 (26.85) | 5.8 (5.37) | 14.5 (23.57) |
| Postdose | 9.0 (8.76) | 32.9 (30.14) | 19.6 (29.51) |

TABLE E

Visual analog scale (VAS) results for "feeling sedated"

| Timepoint | Placebo (mean[SD]) | Cohort A (1:8) (mean[SD]) | Cohort B (1:1) (mean[SD]) |
|---|---|---|---|
| Day 1 Predose | 5.3 (9.24) | 17.5 (26.98) | 3.0 (4.96) |
| Postdose | 36.5 (38.73) | 60.4 (28.73) | 34.3 (31.51) |
| Day 2 Predose | 5.5 (6.61) | 11.5 (12.80) | 13.8 (15.42) |
| Postdose | 6.3 (6.75) | 48.9 (28.69) | 37.8 (31.21) |

TABLE E-continued

Visual analog scale (VAS) results for "feeling sedated"

| Timepoint | Placebo (mean[SD]) | Cohort A (1:8) (mean[SD]) | Cohort B (1:1) (mean[SD]) |
|---|---|---|---|
| Day 3 Predose | 5.5 (5.32) | 8.2 (8.64) | 21.6 (27.76) |
| Postdose | 4.5 (3.87) | 49.0 (32.63) | 31.2 (29.48) |
| Day 4 Predose | 5.8 (6.02) | 12.2 (15.80) | 22.4 (25.55) |
| Postdose | 2.8 (2.22) | 38.4 (34.01) | 22.2 (24.54) |
| Day 5 Predose | 4.0 (3.56) | 9.5 (13.69) | 13.9 (18.05) |
| Postdose | 30.0 (34.55) | 37.0 (31.65) | 20.2 (23.79) |
| Day 6 Predose | 9.8 (14.93) | 6.5 (5.68) | 10.6 (14.65) |
| Postdose | 21.3 (25.62) | 44.8 (31.26) | 19.5 (24.77) |
| Day 7 Predose | 10.8 (10.53) | 17.0 (21.21) | 9.7 (12.91) |
| Postdose | 5.3 (3.77) | 30.3 (25.12) | 14.5 (24.22) |

Bioanalytical method used for determining the $C_{max}$ for Compound-1: A method was validated for measuring Compound-1 in human plasma (K2EDTA). Samples were analyzed using a 50 µL aliquot volume and a protein-precipitation extraction procedure followed by liquid chromatography/tandem mass spectrometry (LC/MS/MS). Compound-1 concentrations were calculated with a $1/x^2$ linear regression over a concentration range of 0.250 to 100 ng/mL using naltrexone-d3 as an internal standard. Ten-fold dilution was successfully tested at 400 ng/mL for both analytes. The API 5000 was operated in the Selected Reaction Monitoring (SRM) mode under optimized conditions for detection of Compound-1, naltrexone-d3 positive ions formed by electrospray ionization.

Bioanalytical method used for determining the $C_{max}$ for buprenorphine: A method was validated for measuring buprenorphine in human plasma (K2EDTA). Samples were analyzed using a 400 µL aliquot volume and a solid-phase extraction procedure followed by liquid chromatography/tandem mass spectrometry (LC/MS/MS). Buprenorphine concentrations were calculated with a $1/x^2$ linear regression over a concentration range of 0.250 to 100 ng/mL. The API 5000 was operated in the Selected Reaction Monitoring (SRM) mode under optimized conditions for detection of buprenorphine and buprenorphine-d4 positive ions formed by electrospray ionization.

The [$^{35}$S]GTPγS assay measures the functional properties of a compound by quantifying the level of G-protein activation following agonist binding in studies using stably transfected cells, and is considered to be a measure of the efficacy of a compound. Membranes from CHO (Chinese Hamster Ovary) cells that stably expressed the cloned human µ opioid receptor were used in the experiments. In a final volume of 0.5 mL, 12 different concentrations of Compound-1 were incubated with 7.5 µg of CHO cell membranes that stably expressed the human µ opioid receptor. The assay buffer consisted of 50 mM Tris-HCl, pH 7.4, 3 mM $MgCl_2$, 0.2 mM EGTA, 3 µM GDP, and 100 mM NaCl. The final concentration of [35S]GTPγS was 0.080 nM. Nonspecific binding was measured by inclusion of 10 µM GTPγS. Binding was initiated by the addition of the membranes. After an incubation of 60 min at 30° C., the samples were filtered through Schleicher & Schuell No. 32 glass fiber filters. The filters were washed three times with cold 50 mM Tris-HCl, pH 7.5, and were counted in 2 mL of Ecoscint scintillation fluid. Data are the mean Emax and $EC_{50}$ values±S.E.M. For calculation of the Emax values, the basal [35S]GTPγS binding was set at 0%, and the 100% [35S]GTPγS binding level was set at the maximum binding achieved with DAMGO.

Example 2

Experiments were conducted in rats to assess the ability of opioid antagonists to modulate buprenorphine-induced dopamine efflux in the Nucleus Accumbens shell (NAc-sh) region of the mesolimbic region of the brain. Male rats weighing 300-400 grams were used for all studies. To measure the efflux of dopamine in the NAc-sh an in vivo microdialysis method was utilized in free-moving rats. This method allows the sampling of extracellular cerebrospinal fluid (CSF) from specific brain regions of interest and measurement of neurotransmitter concentrations following the analysis of sampled dialysate with HPLC-EC.

Each rat underwent surgical implantation of microdialysis guide cannula (CMA 12, CMA Microdialysis) to facilitate the insertion of the microdialysis probe later on. Rats were anesthetized with a mixture of ketamine/xylazine (80/6 mg/kg IP) and placed in a stereotaxic apparatus. Using bregma and skull as reference points, final coordinates were determined by The Rat Brain in Stereotaxic Coordinates (Paxinos and Watson, 2006) for the nucleus accumbens shell (+1.7 A/P, +−0.80 M/L, −7.8 D/V) and the guide cannula were lowered vertically into position (D/V=−5.8 from the skull) and fixed to the skull with glass-ionomer dental acrylic. Guide cannula were capped with dummy probes until microdialysis probe insertion. On the day prior to experimentation (3-4 days post-surgery), animals were weighed to determine appropriate dose for test articles. A microdialysis probe (CMA 12, 2 mm membrane, CMA microdialysis) was then inserted through the guide cannula. Microdialysis probes were connected to a tether system allowing free movement and sterile artificial CSF (aCSF) (CMA microdialysis) was pumped via microsyringe pumps at a rate of 0.25 µL/min through the probe overnight for approximately 16 hours prior to experimentation. On the day following probe insertion, sterile aCSF perfusion was increased to 2.0 µl/min and a pre-baseline equilibration period was established for at least 1.5 hours prior to initiating continuous collection of CSF. After the equilibration period a baseline neurotransmitter levels were determined for each animal over 1.75 hours. Following this baseline period, antagonist plus buprenonorphine (0.1 mg/kg, SC) were administered and continuous sampling of the microdialysate conducted for an additional 4.25 hours. While continuously collected, the CSF was automatically fractioned into 15 minute periods using a chilled microfraction collector for the entire 6.0 hours collection period (1.75 baseline phase and 4.25 hour treatment phase). Each sample was analyzed via HPLC-EC to determine neurotransmitter concentration of dopamine based upon a six-point standard curve. The average dopamine per sample over the 4.25 treatment phase was used in all comparisons among treatment groups.

Figure 2:
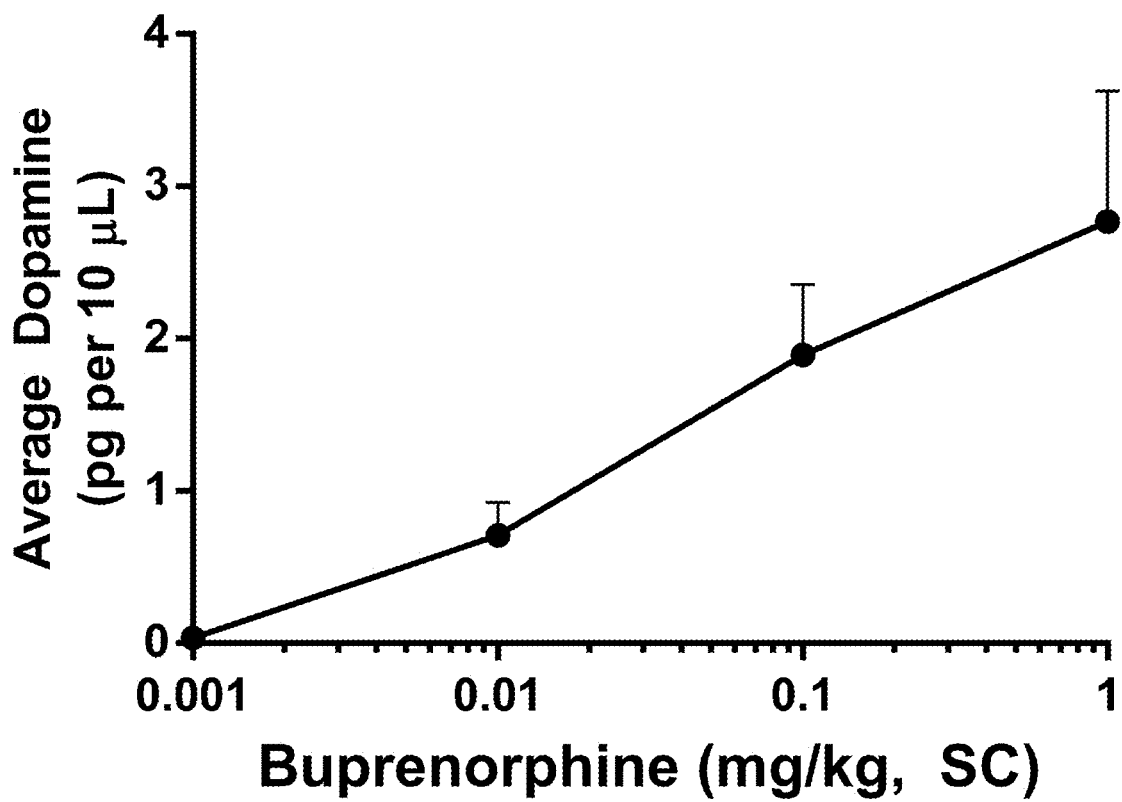
FIG. 2: Average dopamine efflux following (SC) administration of buprenorphine at increasing doses.
Figure 3:
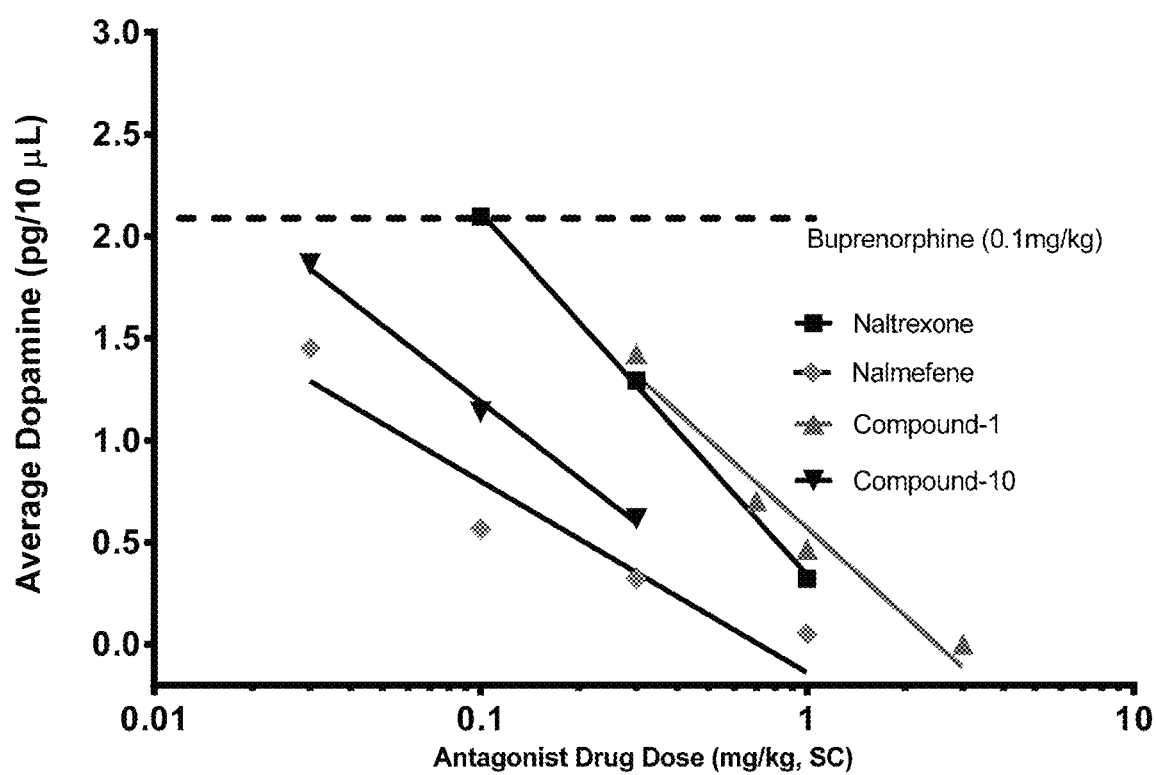
FIG. 3: Reduction in the efflux of dopamine in nucleus accumbens shell following administration of Compound-1, Compound-10, naltrexone and nalmefene with Buprenorphine (0.1 mg/kg).
Figure 4:
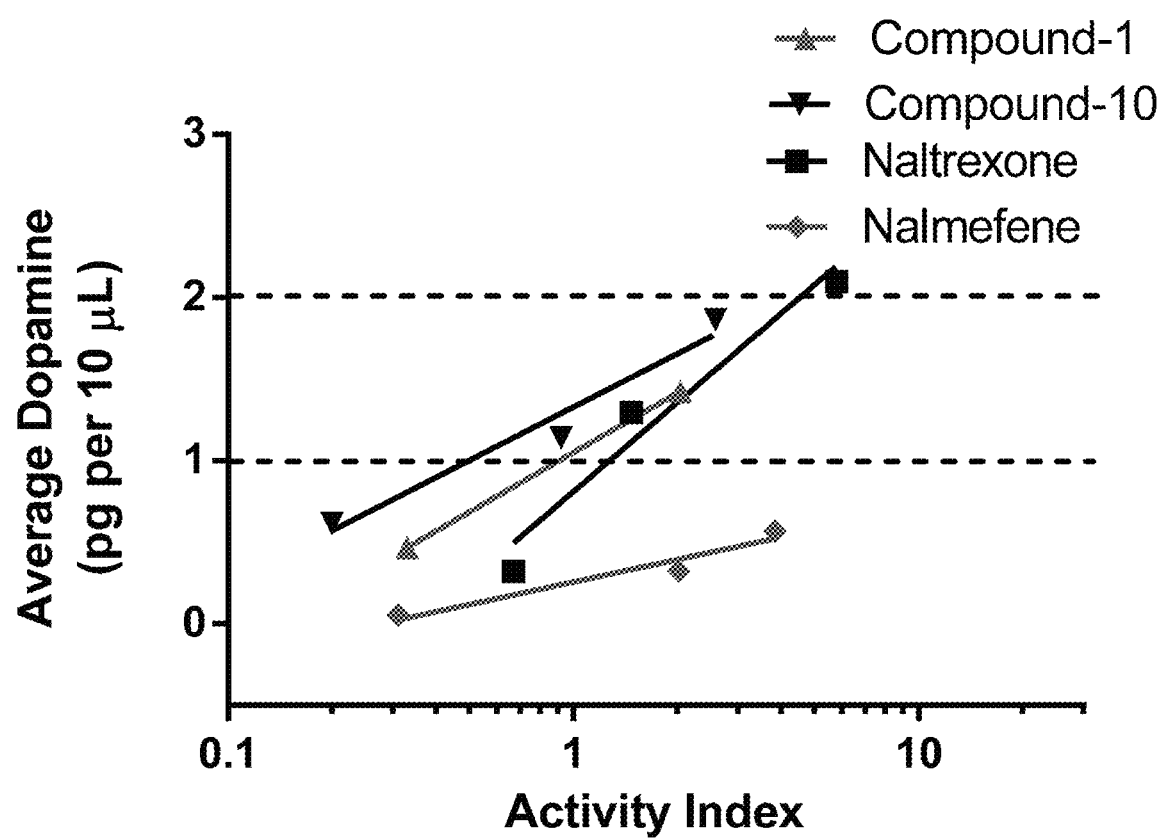
FIG. 4: Log Activity Index (Log AAnAI) versus dopamine efflux for Compound-1, Compound-10, naltrexone and nalmefene with Buprenorphine (0.1 mg/kg).

In rats buprenorphrine resulted in dose dependent increases in NAc-sh dopamine efflux between doses of 0.01 and 1 mg per kg (FIGS. 1 and 2). At doses of 0.1 and 1.0 mg per kg behavioral effects of buprenorphine were observed, including initial sedation followed by hyperactivity. Consequently all additional experiments with µ opioid antagonist used a dose of 0.1 mg per kg of buprenorphine since it represented the lowest dose associated with clear behavioral effects. As shown in FIG. 3 each of the four antagonists evaluated resulted in linear dose-dependent decreases in NAc-sh dopamine efflux. However, the range in apparent potencies was considerable. Based on the AAnAI concept, this result was expected since neither differences in potency at the μ opioid receptor or in the pharmacokinetic properties of the antagonists is taken into account.

TABLE F $C_{max}$ values for Compound-1, Compound-10, naltrexone and nalmefene with Buprenorphine (0.1 mg/kg)

| Antagonist | Dose of Antagonist mg per kg | | | |
|---|---|---|---|---|
| | 0.03 | 0.1 | 0.3 | 1.0 |
| Compound-1 | — | — | 11.8 | 75.5 |
| Compound-10 | 2.24 | 18.1 | 29.5 | — |
| Naltrexone | — | 19.27 | 76.9 | 169 |
| Nalmefene | — | 14.13 | 25.6 | 162 |

Example 3

The AAnAI concept was applied to the study results obtained where NAc-sh dopamine efflux was attenuated with increasing doses of the four μ-opioid receptor antagonist antagonists. Due to the inherent minor stress associated with PK sampling, and the sensitivity of neural chemistry to this stress, different groups of animals were required to establish circulating concentrations of buprenorphine and the antagonists at each dose level evaluated. Male rats weighing between 300-400 grams, the same weight range used in the microdialysis studies, were used for these PK experiments. Since all animals received a fixed dose of buprenorphine, a commercial formulation of buprenorphine (Buprenex (Reckitt Benckiser)) was diluted to 0.1 mg/ml with sterile saline and then used as the vehicle for the required doses of Compound 1, Compound-10, naltrexone and nalmefene. This approached ensured that at each dose of the antagonist studied the concomitant dose of buprenorphrine would be 0.1 mg per kg. All injections were made by the subcutaneous route at the doses indicated in Table G. Sterile solutions of the test formulations (combination of antagonist with 0.1 mg/kg buprenorphine) were given subcutaneously (designated as time 0). Sample of blood were collected at 5, 15, 30, 60 and 120 minutes post dosing. For each blood sampling time point, rats were lightly anesthetized using (3%) isoflourane anesthesia and approximately 200 μl of blood was withdrawn from the lateral tail vein using a 27.5 gauge needle and placed into chilled K2 EDTA tubes. The collection tubes were inverted 10-15 times and then held on ice prior to centrifugation. Plasma was obtained by centrifuging samples for 2 minutes at 14,000×g (11,500 RPM using Eppendorf 5417R centrifuge rotor) at 4° C. The harvested samples of plasma were frozen at −80° C. until assayed for buprenorphine and the antagonists (Compound 1, Compound 10, naltrexone or nalmefene). The $C_{max}$ values for each antagonist at the doses evaluated are shown in Table F. These values were used to calculate the AAnAI index associated with reductions in NAc-sh DA with increasing administered doses of the antagonist, taking into account differences in potency and PK properties among these compounds. As can be seen from FIG. 3, the variability in the NAc-sh dopamine shown in Table E across the antagonist was essentially eliminated for Compound 1, Compound-10 and naltrexone by taking into account the in vitro potency and the $C_{max}$ achieved. Nalmefene did appear more potent in attenuating buprenorphine-induced NAc-sh dopamine efflux, indicating that in rats other factors may influence the NAc-sh dopamine response to nalmefene.

TABLE G

Calculated AAnAI values for varying doses of Compound-1, Compound-10, naltrexone and nalmefene with Buprenorphine (0.1 mg/kg)

| Antagonist | Antagonist $IC_{50}$ (nM) | Dose of Antagonist mg per kg | | | |
|---|---|---|---|---|---|
| | | 0.03 | 0.1 | 0.3 | 1.0 |
| Compound-1 | 0.9 | — | — | 2.04 | 0.33 |
| Compound-10 | 0.23 | 2.58 | 0.92 | 0.2 | — |
| Naltrexone | 4.8 | — | 5.79 | 1.47 | 0.67 |
| Nalmefene | 13 | — | 3.83 | 2.02 | 0.31 |

Example 4

Figure 5:
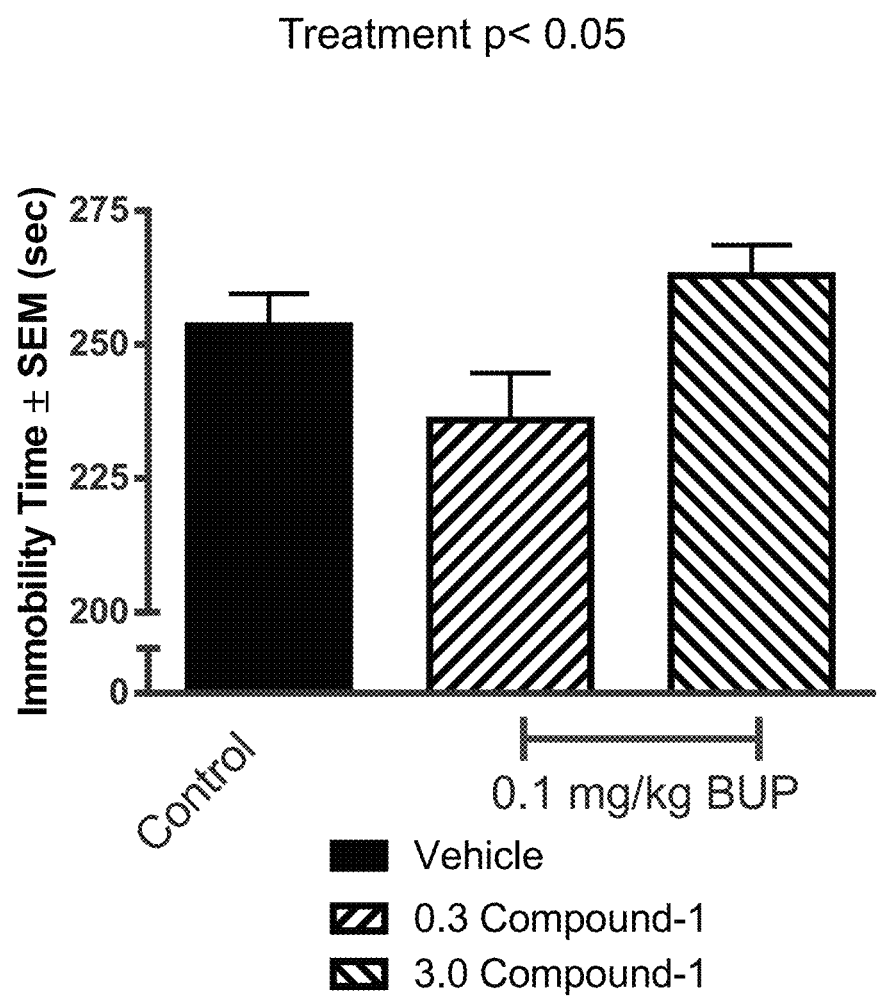
FIG. 5: Increase in immobility following increased concentrations of Compound-1 in forced swim test in WKY rats treated with Buprenorphine (0.1 mg/kg).
Figure 6:
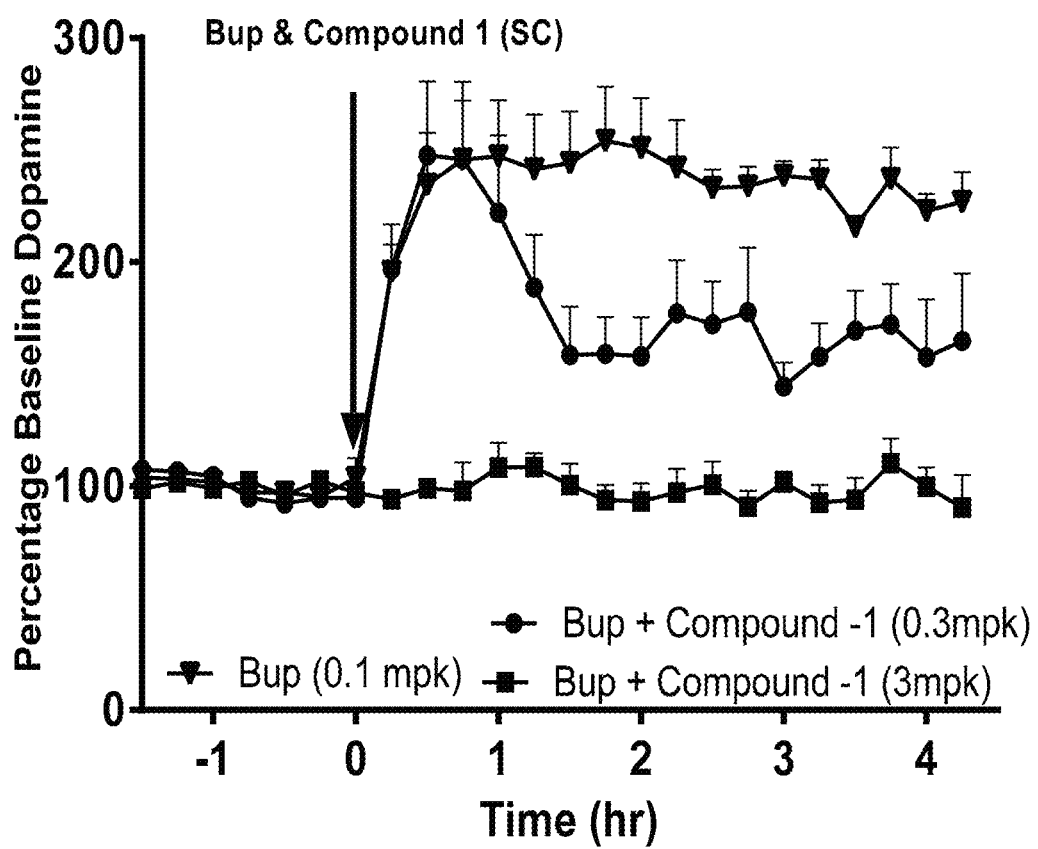
FIG. 6: The effect of Compound-1 on dopamine efflux in WKY rats undergoing forced swim test after treatment with Buprenorphine (0.1 mg/kg).
Figure 7:
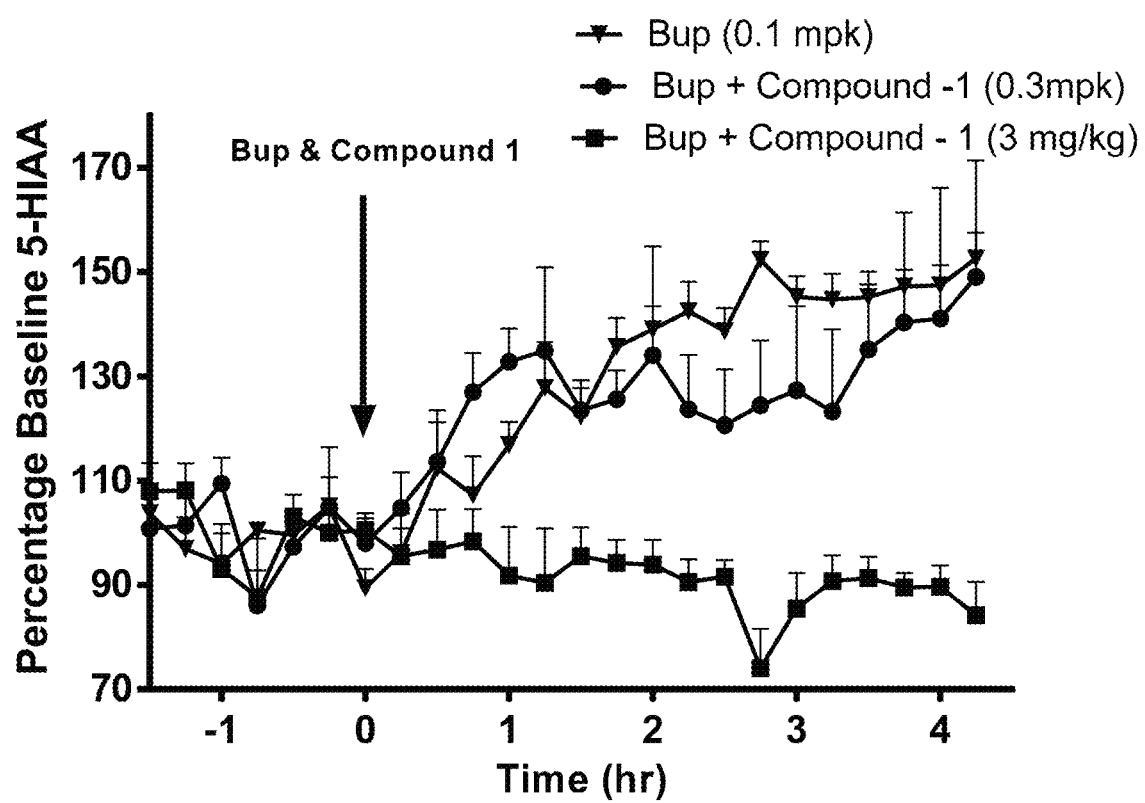
FIG. 7: The efflux of Compound-1 on 5-Hydroxyindoleacetic acid (5-HIAA) release in WKY rats undergoing the forced swim test after treatment with Buprenorphine (0.1 mg/kg).

The desired range of the AAnAI to achieve a clinical anti-depressive effect is between values of about 0.5 and 5, and preferably about 0.7 and 2.2. These ranges take into account the inherent variability in assay methods used to experimentally determine values for the $EC_{50}$ of buprenorphine and its concentration in plasma, and the $IC_{50}$ of opioid antagonists and their concentrations in plasma for both non-clinical and clinical studies. As cited in Example 1, with plasma $C_{max}$ values for buprenorphine and Compound 1 resulting in AAnAI values of greater than 5, patients reported experiencing greater subjective feelings of high and sedation; undesirable traits for a buprenorphine and opioid antagonist combination intended for the treatment of depression. In the "forced swim test" (FST) rats are placed in a tank of water, from which they cannot escape, on two successive days; 15 minutes on the first day and 5 minutes on the second day. While in the water they will swim, attempt to climb the container wall or become "immobile" floating in the water. The total time rats are immobility increases between the first and second day. Drugs that have antidepressant effects in humans reduce immobility time on day 2 and this model is frequently used to evaluate potential anti-depressive like activity of drugs. Strain of rat can also affect total immobility time, with the Wistar-Kyoto (WKY) strain showing high immobility times. The WKY rat is spontaneously hypertensive and displays hormonal and depressive-like behavioral abnormalities. To explore the lower end of the range of the AAnAI, an experiment was conducted using three groups of rats in the FST paradigm. Rats received three separate subcutaneous injections of either vehicle alone or a combination of buprenorphine (0.1 mg/kg) and Compound-1 (0.3 or 3.0 mg/kg) at 1, 19, and 23 h after the first exposure to the swim tanks. At 24 h after the first swim, rats were retested for 5 minutes. Videos were scored manually for immobility time (in seconds) using a manual stop watch in 60 second intervals by a rater blinded to the treatment groups. A rat was judged to be immobile if it was making only movements necessary to keep its head above water. Results for this study are shown in FIG. 5. Immobility time was significantly lower (p<0.05) in rats given the combination of buprenorphine and Compound 1 at 0.3 mg/kg, indicating an anti-depressive like action. An AAnAI value of approximately 2 was associated with this dose combination of buprenorphine and Compound 1. The anti-depressive like effect of the combination was lost when the dose of antagonist was raised to 3.0 mg/kg when an AAnAI of less than 0.3 was achieved. These data, along with the clinical data shown in Example 1 illustrate the importance of both the upper and lower boundaries of the AAnAI in order to achieve an anti-depressant activity without undesired side effects. FIGS. 6 and 7, show the complete attenuation of buprenorphine effects at the highest dose of Compound 1 for NAc-sh dopamine and 5-HIAA. These data further illustrate that at the desirable dose combination effects of buprenorphine are being modulated, but not eliminated, by Compound 1.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of treating a depressive disorder comprising administering a composition comprising about 2 mg to about 25 mg of buprenorphine and a therapeutically effective amount of Compound-1 to a patient in need thereof, wherein Compound-1 has the structure:

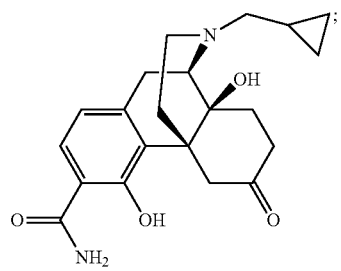 [SMILES: NC(=O)c1ccc2c(c1O)[C@]13CCN(CC4CC4)[C@H](C2)[C@]1(O)CCC(=O)C3]

and
wherein said depressive disorder is selected from major depressive disorder, chronic depression, severe unipolar recurrent major depressive episodes, dysthymic disorder, depressive neurosis and neurotic depression, melancholic depression, atypical depression, reactive depression, treatment resistant depression, seasonal affective disorder and pediatric depression; premenstrual syndrome, premenstrual dysphoric disorder, hot flashes, bipolar disorders or manic depression, bipolar I disorder, bipolar II disorder and cyclothymic disorder.

2. The method according to claim 1, wherein said depressive disorder is major depressive disorder.

3. The method according to claim 1, comprising about 1.0 to about 20 mg of Compound-1.

4. The method according to claim 1, comprising about 1.0 to about 10 mg of Compound-1.

5. The method according to claim 1, comprising about 1.0 to about 8 mg of Compound-1.

6. The method according to claim 1, comprising about 1.0 to about 4 mg of Compound-1.

7. The method according to claim 1, comprising about 2 mg of Compound-1.

8. The method according to claim 1, comprising about 2 mg to about 8 mg of buprenorphine.

9. The method according to claim 1, comprising about 2 mg to about 4 mg of buprenorphine.

10. The method according to claim 1, comprising about 2 mg of buprenorphine.

11. A method of treating a depressive disorder comprising administering a composition comprising about 0.5 mg to about 20 mg of Compound-1 and a therapeutically effective amount of buprenorphine to a patient in need thereof, wherein Compound-1 has the structure:

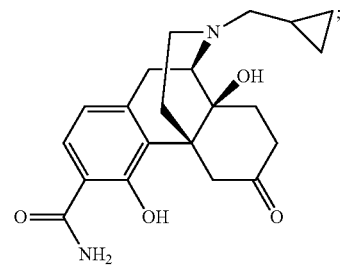 [SMILES: NC(=O)c1ccc2c(c1O)[C@]13CCN(CC4CC4)[C@H](C2)[C@]1(O)CCC(=O)C3]

and
wherein said depressive disorder is selected from major depressive disorder, chronic depression, severe unipolar recurrent major depressive episodes, dysthymic disorder, depressive neurosis and neurotic depression, melancholic depression, atypical depression, reactive depression, treatment resistant depression, seasonal affective disorder and pediatric depression; premenstrual syndrome, premenstrual dysphoric disorder, hot flashes, bipolar disorders or manic depression, bipolar I disorder, bipolar II disorder and cyclothymic disorder.

12. The method according to claim 11, wherein said depressive disorder is major depressive disorder.

13. The method according to claim 11, comprising about 1.0 to about 10 mg of Compound-1.

14. The method according to claim 11, comprising about 1.0 to about 8 mg of Compound-1.

15. The method according to claim 11, comprising about 1.0 to about 4 mg of Compound-1.

16. The method according to claim 11, comprising about 2 mg of Compound-1.

17. The method according to claim 11, comprising about 2 mg to about 50 mg of buprenorphine.

18. The method according to claim 11, comprising about 2 mg to about 8 mg of buprenorphine.

19. The method according to claim 11, comprising about 2 mg to about 4 mg of buprenorphine.

20. The method according to claim 11, comprising about 2 mg of buprenorphine.

* * * * *